United States Patent

Daugherty et al.

[11] Patent Number: 5,733,308
[45] Date of Patent: Mar. 31, 1998

[54] SURGICAL PLEDGET DISPENSING SYSTEM

[75] Inventors: John R. Daugherty; Paul D. Diegel; Bret J. Kilgrow, all of Flagstaff, Ariz.

[73] Assignee: W. L. Gore & Associates, Inc., Newark, Del.

[21] Appl. No.: 811,859

[22] Filed: Mar. 5, 1997

Related U.S. Application Data

[63] Continuation of Ser. No. 426,803, Apr. 21, 1995, abandoned.
[51] Int. Cl.⁶ .................. A61B 17/04; B65D 85/24
[52] U.S. Cl. .................. 606/232; 606/228; 606/151; 206/343; 206/345; 206/339; 206/820
[58] Field of Search .................. 606/215, 216, 606/213, 212, 220, 148, 232, 228; 221/6; 206/339, 343, 345, 820

[56] References Cited

U.S. PATENT DOCUMENTS

| | | | |
|---|---|---|---|
| 2,884,150 | 4/1959 | Weichselbaum et al. | 206/820 |
| 3,550,856 | 12/1970 | Wise | 206/820 |
| 4,034,850 | 7/1977 | Mandel et al. | |
| 4,187,390 | 2/1980 | Gore | 174/102 R |
| 4,200,190 | 4/1980 | Tyson | 206/820 |
| 4,398,327 | 8/1983 | Yamazaki . | |
| 4,478,665 | 10/1984 | Hubis | 156/229 |
| 4,548,202 | 10/1985 | Duncan | 606/220 |
| 4,549,545 | 10/1985 | Levy | 606/228 |
| 4,674,629 | 6/1987 | Lunselmn . | |
| 4,823,794 | 4/1989 | Pierce | 606/151 |
| 4,898,155 | 2/1990 | Ovil et al. . | |
| 4,946,386 | 8/1990 | Kidd et al. | 206/820 |
| 5,078,730 | 1/1992 | Li . | |
| 5,141,522 | 8/1992 | Landi . | |
| 5,219,359 | 6/1993 | McQuilkin et al. . | |
| 5,230,424 | 7/1993 | Alpern . | |
| 5,263,970 | 11/1993 | Preller | 606/216 |
| 5,307,924 | 5/1994 | Manosalva . | |

FOREIGN PATENT DOCUMENTS

| | | | |
|---|---|---|---|
| 0168172 | 1/1986 | European Pat. Off. . | |
| 0476956 | 3/1992 | European Pat. Off. . | |
| 0492172 | 7/1992 | European Pat. Off. . | |
| 0494637 | 7/1992 | European Pat. Off. . | |
| 927236 | 5/1982 | U.S.S.R. | 606/218 |

*Primary Examiner*—Gary Jackson
*Attorney, Agent, or Firm*—Wayne D. House

[57] ABSTRACT

A surgical pledget dispensing system wherein a pledget is affixed to at least one other object whereby the pledget is tearably releasable from the at least one other object. Preferably a multiplicity of pledgers are affixed to the at least one other object in a tearably releasable fashion. The at least one other object is preferably at least one runner, a portion of a suture package or at least one other pledget.

34 Claims, 4 Drawing Sheets

SURGICAL PLEDGET DISPENSING SYSTEM

This application is a continuation, of application Ser. No. 08/426,803 filed Apr. 21, 1995, now abandoned.

FIELD OF INVENTION

The present invention relates to the field of surgical pledgets and dispensing systems therefor.

BACKGROUND OF THE INVENTION

Surgical pledgets are small pieces of biocompatible material that are typically used in conjunction with surgical sutures to distribute the retaining force of the suture over a larger area of tissue or to aid in stemming the leakage of bodily fluids such as blood that results from penetration of bodily tissue by a suture needle and suture. Pledgets have been used routinely almost from the initial use of sutures to repair tissues. In some situations the pledgets may be left implanted permanently in living bodies; in other situations they are removed along with the sutures from the living body.

Pledgets generally take the form of small ovoid, oblong or circular shapes made from biocompatible sheet materials typically having one or two small, pre-formed holes through the sheet just large enough to accommodate a suture of the desired size. Materials used previously to make pledgets include polyamide, polyethylene, polypropylene, polyethylene terephthalate, polyurethane, polytetrafluoroethylene (hereinafter PTFE), various bioresorbable polymers and small pieces of autologous tissue.

U.S. Pat. No. 4,823,794 to Pierce describes pledgets generally and in particular describes pledgets having a slit between a suture hole and an adjacent edge of the pledget.

Heretofore, pledgets have been dispensed by packaging quantities of them into a sealed container which allows the pledgets to be maintained in a sterile condition. The individual pledgets within the container are not connected to each other in any fashion. The container is opened within the operating room and the pledgets are removed individually when needed by picking them up with forceps. Using a needle-driver, a suture needle and suture are inserted through the pledget while the pledget is held by the forceps. The process is repeated when a second pledget is removed from the same container in the same fashion.

SUMMARY OF THE INVENTION

The present invention relates to a surgical pledget dispensing system comprising a pledget affixed to at least one other object whereby the pledget is tearably releasable from the at least one other object. Preferably the surgical pledget dispensing system comprises a multiplicity of pledgets affixed to at least one other object whereby each pledget is individually tearably releasable from the at least one other object. A multiplicity of pledgets is defined herein as meaning two or more pledgets. The at least one other object is preferably at least one runner, a portion of a suture package or at least one other pledget.

DETAILED DESCRIPTION OF THE INVENTION

Figure 1:
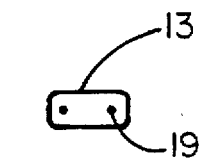
FIG. 1 describes a surgical pledget of the prior art.

FIG. 1 describes a typical pledget of the prior art. The pledget 13 shown here is an oblong shape cut or formed from a sheet of biocompatible material. The pledget 13 has, in this instance, two small suture holes 19 through which a suture may be inserted via a suture needle.

Figure 2:
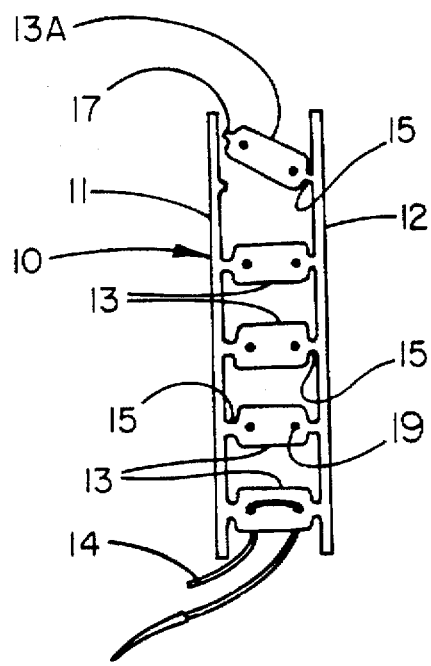
FIG. 2 describes a surgical pledget dispensing system having two runners where each end of each pledget is affixed to a runner whereby each end of the pledget is tearably releasable from the runner.

The suture dispensing system of the present invention is described by FIG. 2. At least one pledget 13 is connected to runners 11 and 12 in a fashion that allows each individual pledget 13 to be tearably released from runners 11 and 12 at connection points 15. Pledget 13A has been tearably released at end 17 from runner 11; the opposite end of pledget 13A is releasable in the same fashion as are both ends of the other pledgets 13. The release is accomplished by simply gripping the pledget to be released in a forceps while gripping the runner in another forceps and pulling the two forceps in opposite directions. Alternatively and preferably the release is accomplished by first gripping one or both of the runners the pledget is affixed to using a forceps, threading the suture hole of the pledget with the suture with which it is intended to be used, and tearably releasing the pledget from the runner or runners by pulling the pledget via the suture 14 in an opposite direction from the forceps.

Figure 3A:
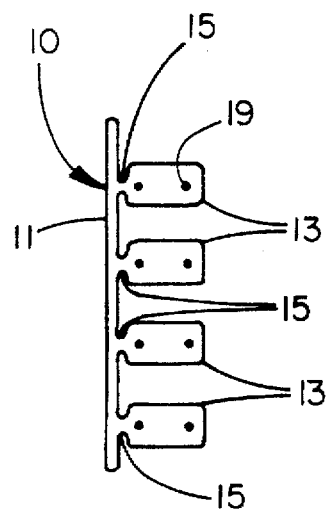
FIGS. 3A & 3B describe a surgical pledget dispensing system whereby the pledgets are affixed in a tearably releasable fashion to a single runner.
Figure 3B:
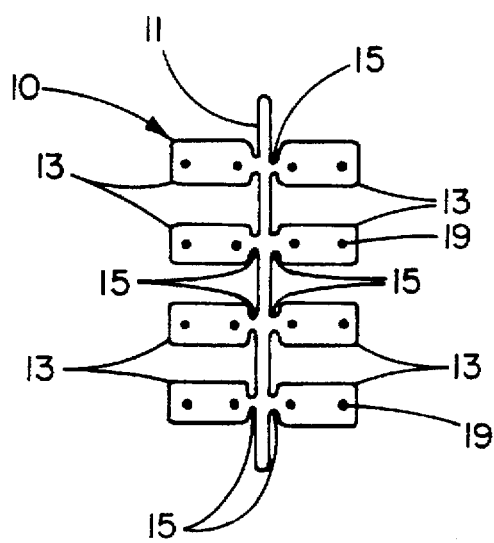

FIGS. 3A and 3B describe alternative embodiments of the pledget dispensing system. FIG. 3A shows a group of pledgets 13 affixed to one side of a runner 11; FIG. 3B shows two groups of pledgets 13 affixed to a single runner 11 with the two groups affixed to opposite sides of the runner 11.

Figure 4:
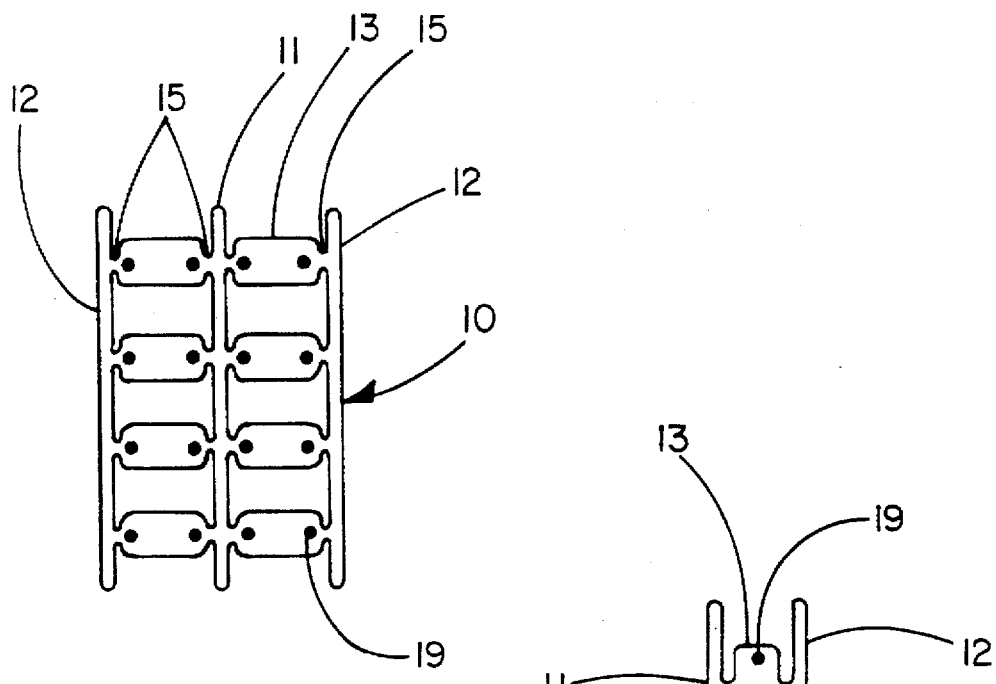
FIG. 4 describes a surgical pledget dispensing system whereby two groups of pledgets are affixed to a middle runner and the opposite ends of each group of pledgets is affixed to a separate runner.

FIG. 4 describes an alternative embodiment whereby two groups of pledgets 13 are affixed to a common runner 11 with the opposite ends of each group of pledgets affixed to an additional runner 12.

Figure 5:
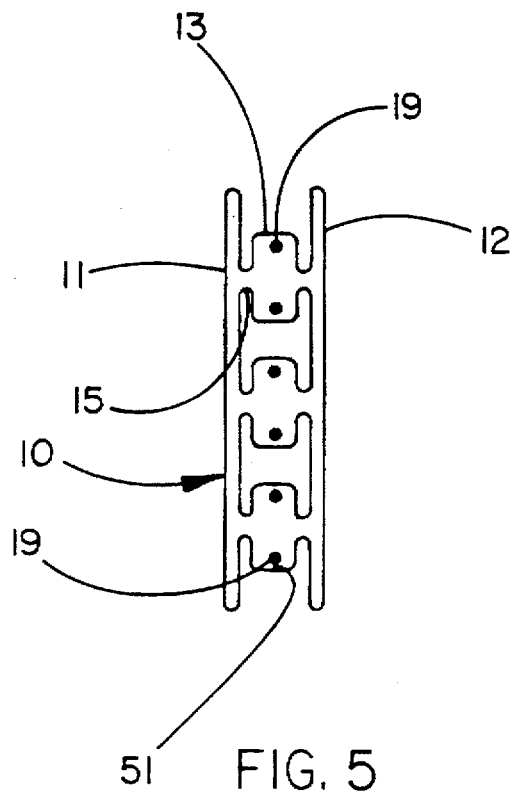
FIG. 5 describes a surgical pledget dispensing system whereby the sides of the pledgets are affixed to runners.

As shown by FIG. 5, the pledgets 13 may be affixed to the runners 11 and 12 at their sides rather than at their ends. This method allows the use of access slits 51 in the ends of the pledgets 13 between the end edge and the suture access hole 19 for ease of attaching a suture to the pledget. The use of access slits 51 is not, however, limited to being located at only the end of the pledget 13.

Figure 6:
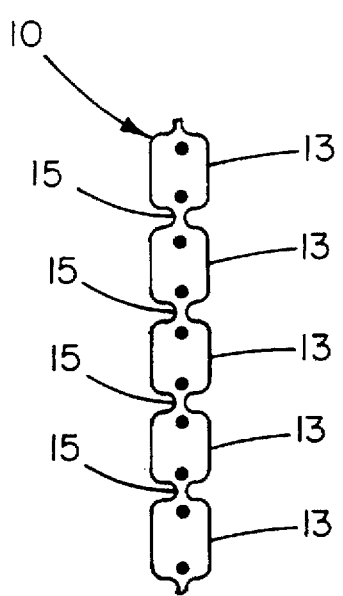
FIG. 6 describes a surgical pledget dispensing system whereby the pledgets are affixed to each other in a tearably releasable fashion.

FIG. 6 describes an alternative embodiment wherein adjacent pledgets 13 are affixed to each other at connection points 15 whereby the adjacent pledgets 13 may be tearably released from each other.

Figure 7:
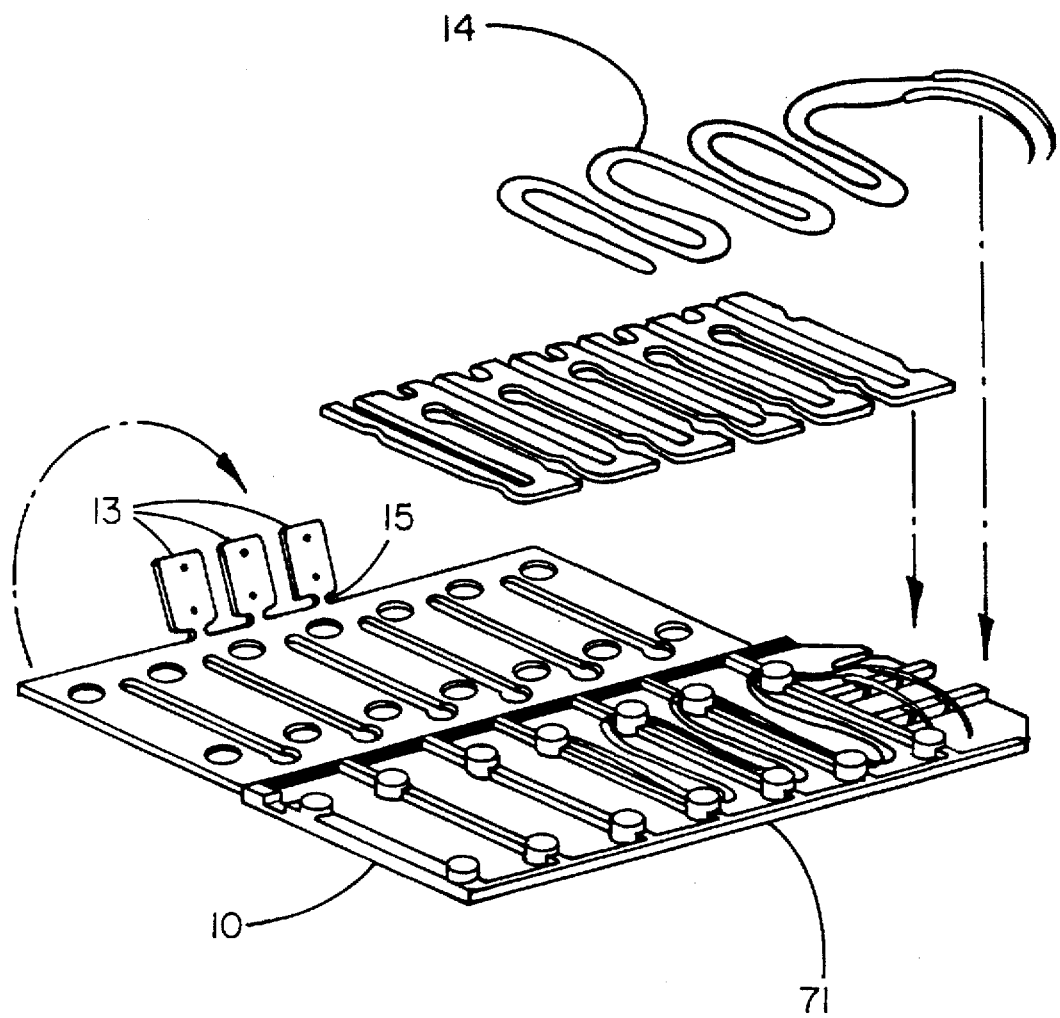
FIG. 7 describes a surgical pledget dispensing system whereby the pledgets are affixed to a portion of a suture package.
Figure 8:
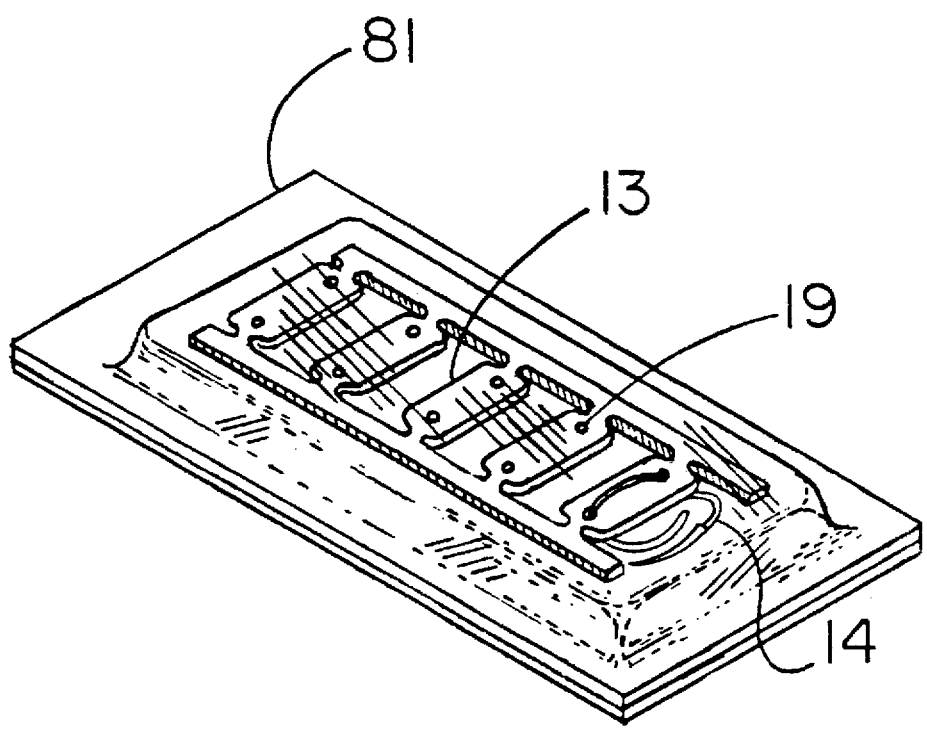
FIG. 8 describes the pledgets enclosed in a package.

FIG. 7 describes a suture pledget dispensing system 10 having at least one pledget 13 affixed to a portion of a suture package 71 whereby the at least one pledget is tearably releasable from the portion of the suture package. The pledgets may be affixed to any portion of the suture package including the package itself, an envelope enclosing the package, a separate card which is a part of a package, or a package lid. The pledget itself must be made from a biocompatible material suitable for the particular surgical repair requiring the pledget. FIG. 8 describes the pledgets 13 of the present invention contained in an enclosing package 81. They may be provided in sterile form within the package 81; packages of this type are well known in the art. The package 81 may also contain sutures 14 in addition to pledgets 13; the sutures 14 may optionally be provided pre-threaded through the pledget holes 19.

It is apparent that various methods may be used to manufacture the pledget dispensing system. The particular method chosen is most likely to depend on the material selected for the pledgets. They may be made by, for example, injection molding or cutting by stamping.

Regardless of the material chosen, the runners 11 and 12 must be made to be stronger than the point of attachment 15 so that the runners do not break when the pledget 13 is tearably released from the runners 11 or 12 at the connection point 15.

In a preferred embodiment, the pledget dispensing system including pledgets is made from porous, expanded PTFE having a microstructure of nodes interconnected by fibrils. Materials of this type are made as taught by U.S. Pat. No. 4,187,390 to Gore and U.S. Pat. No. 4,478,665 to Hubis. A suitable material is GORE-TEX® Surgical Membrane (W. L. Gore & Associates, Inc., Flagstaff, Ariz.). Materials of this type are preferred because they are flexible, strong, lubricious and highly biocompatible. The pledget dispensing system can readily be cut from such a material using a programmable laser cutting system programmed to cut the desired pattern. The suture holes through the pledgets may be cut by the same method. A suitable laser cutting system is Model No. ULS 1720C from Universal Laser Systems, Inc., Scottsdale, Ariz.

While particular embodiments of the present invention have been illustrated and described herein, the present invention should not be limited to such illustrations and descriptions. It should be apparent that changes and modifications may be incorporated and embodied as part of the present invention within the scope of the following claims.

We claim:

1. A surgical pledget dispensing system comprising a surgical pledget affixed to at least one other object whereby said pledget is tearably releasable from the other object, wherein said surgical pledget dispensing system is contained in a sterile condition in a sealed container.

2. A surgical pledget dispensing system according to claim 1 wherein the pledget is comprised of biocompatible materials selected from the group consisting of polyamide, polyethylene, polypropylene, polyethylene terephthalate, polyurethane, polytetrafluoroethylene and resorbable polymers.

3. A surgical pledget dispensing system according to claim 2 wherein the polytetrafluoroethylene is porous polytetrafluoroethylene.

4. A surgical pledget dispensing system according to claim 3 wherein the porous polytetrafluoroethylene has a microstructure of nodes interconnected by fibrils.

5. A surgical pledget dispensing system according to claim 1 wherein the at least one other object comprises at least one runner.

6. A surgical pledget dispensing system according to claim 5 wherein the at least one runner comprises two runners.

7. A surgical pledget dispensing system according to claim 5 wherein the pledget is comprised of biocompatible materials selected from the group consisting of polyamide, polyethylene, polypropylene, polyethylene terephthalate, polyurethane, polytetrafluoroethylene and resorbable polymers.

8. A surgical pledget dispensing system according to claim 7 wherein the polytetrafluoroethylene is porous polytetrafluoroethylene.

9. A surgical pledget dispensing system according to claim 8 wherein the porous polytetrafluoroethylene has a microstructure of nodes interconnected by fibrils.

10. A surgical pledget dispensing system according to claim 1 wherein the at least one other object comprises a portion of a suture package.

11. A surgical pledget dispensing system according to claim 10 wherein the pledget is comprised of biocompatible materials selected from the group consisting of polyamide, polyethylene, polypropylene, polyethylene terephthalate, polyurethane, polytetrafluoroethylene and resorbable polymers.

12. A surgical pledget dispensing system according to claim 11 wherein the polytetrafluoroethylene is porous polytetrafluoroethylene.

13. A surgical pledget dispensing system according to claim 12 wherein the porous polytetrafluoroethylene has a microstructure of nodes interconnected by fibrils.

14. A surgical pledget dispensing system according to claim 1 wherein the at least one other object comprises another pledget.

15. A surgical pledget dispensing system according to claim 14 wherein the pledget is comprised of biocompatible materials selected from the group consisting of polyamide, polyethylene, polypropylene, polyethylene terephthalate, polyurethane, polytetrafluoroethylene and resorbable polymers.

16. A surgical pledget dispensing system according to claim 15 wherein the polytetrafluoroethylene is porous polytetrafluoroethylene.

17. A surgical pledget dispensing system according to claim 16 wherein the porous polytetrafluoroethylene has a microstructure of nodes interconnected by fibrils.

18. A surgical pledget dispensing system comprising a multiplicity of surgical pledgets affixed to at least one other object whereby said pledgets are individually tearably releasable from the other object, wherein said surgical pledget dispensing system is contained in a sterile condition in a sealed container.

19. A surgical pledget dispensing system according to claim 18 wherein the multiplicity of surgical pledgets is comprised of biocompatible materials selected from the group consisting of polyamide, polyethylene, polypropylene, polyethylene terephthalate, polyurethane, polytetrafluoroethylene and resorbable polymers.

20. A surgical pledget dispensing system according to claim 19 wherein the polytetrafluoroethylene is porous polytetrafluoroethylene.

21. A surgical pledget dispensing system according to claim 20 wherein the porous polytetrafluoroethylene has a microstructure of nodes interconnected by fibrils.

22. A surgical pledget dispensing system according to claim 18 wherein the at least one other object comprises at least one runner.

23. A surgical pledget dispensing system according to claim 22 wherein the multiplicity of surgical pledgets is comprised of biocompatible materials selected from the group consisting of polyamide, polyethylene, polypropylene, polyethylene terephthalate, polyurethane, polytetrafluoroethylene and resorbable polymers.

24. A surgical pledget dispensing system according to claim 23 wherein the polytetrafluoroethylene is porous polytetrafluoroethylene.

25. A surgical pledget dispensing system according to claim 24 wherein the porous polytetrafluoroethylene has a microstructure of nodes interconnected by fibrils.

26. A surgical pledget dispensing system according to claim 18 wherein the at least one other object comprises a portion of a suture package.

27. A surgical pledget dispensing system according to claim 26 wherein the multiplicity of surgical pledgets is comprised of biocompatible materials selected from the group consisting of polyamide, polyethylene, polypropylene, polyethylene terephthalate, polyurethane, polytetrafluoroethylene and resorbable polymers.

28. A surgical pledget dispensing system according to claim 27 wherein the polytetrafluoroethylene is porous polytetrafluoroethylene.

29. A surgical pledget dispensing system according to claim 28 wherein the porous polytetrafluoroethylene has a microstructure of nodes interconnected by fibrils.

30. A surgical pledget dispensing system according to claim 18 wherein the at least one other object comprises another pledget.

31. A surgical pledget dispensing system according to claim 30 wherein the multiplicity of surgical pledgets is comprised of biocompatible materials selected from the group consisting of polyamide, polyethylene, polypropylene, polyethylene terephthalate, polyurethane, polytetrafluoroethylene and resorbable polymers.

32. A surgical pledget dispensing system according to claim 31 wherein the polytetrafluoroethylene is porous polytetrafluoroethylene.

33. A surgical pledget dispensing system according to claim 32 wherein the porous polytetrafluoroethylene has a microstructure of nodes interconnected by fibrils.

34. A surgical pledget dispensing system comprising a surgical pledget affixed to at least one other object whereby said pledget is tearably releasable from the other object, said pledget having a suture hole and having a suture which passes through the suture hole.

* * * * *